United States Patent
Aprigliano Fernandes et al.

(10) Patent No.: US 10,722,449 B2
(45) Date of Patent: Jul. 28, 2020

(54) COSMETIC COMPOSITION COMPRISING AMINO SILICONES, CATIONIC SURFACTANTS AND SPECIFIC ESTERS AND A PROCESS FOR A COSMETIC TREATMENT

(71) Applicant: L'OREAL, Paris (FR)

(72) Inventors: Pedro M. Aprigliano Fernandes, Rio de Janeiro—RJ (BR); Carlos Contreras Granados, Rio de Janeiro—RJ (BR)

(73) Assignee: L'OREAL, Paris (FR)

( * ) Notice: Subject to any disclaimer, the term of this patent is extended or adjusted under 35 U.S.C. 154(b) by 416 days.

(21) Appl. No.: 14/912,799

(22) PCT Filed: Aug. 20, 2013

(86) PCT No.: PCT/BR2013/000314
§ 371 (c)(1),
(2) Date: Feb. 18, 2016

(87) PCT Pub. No.: WO2015/024079
PCT Pub. Date: Feb. 26, 2015

(65) Prior Publication Data
US 2016/0193136 A1    Jul. 7, 2016

(51) Int. Cl.
*A61Q 5/12*    (2006.01)
*A61K 8/898*    (2006.01)
*A61K 8/41*    (2006.01)
*A61Q 5/02*    (2006.01)
*A61K 8/37*    (2006.01)

(52) U.S. Cl.
CPC ............. *A61K 8/898* (2013.01); *A61K 8/37* (2013.01); *A61K 8/416* (2013.01); *A61Q 5/02* (2013.01); *A61Q 5/12* (2013.01); *A61K 8/375* (2013.01); *A61K 2800/5426* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 2006/0013843 A1* | 1/2006 | Shimizu | A61K 8/37 424/401 |
| 2006/0034792 A1* | 2/2006 | Lazzeri | A61K 8/046 424/70.12 |
| 2006/0057096 A1* | 3/2006 | Lazzeri | A61K 8/342 424/70.121 |
| 2007/0190016 A1* | 8/2007 | Pasquet | A61K 8/8182 424/70.122 |
| 2007/0258936 A1 | 11/2007 | Decoster et al. | |
| 2008/0305133 A1* | 12/2008 | Berg-Schultz | A61K 8/11 424/401 |
| 2009/0053161 A1* | 2/2009 | Nguyen | A61K 8/39 424/70.17 |
| 2009/0071493 A1* | 3/2009 | Nguyen | A61K 8/361 132/202 |
| 2010/0086502 A1* | 4/2010 | Lucet-Levannier | A61K 8/35 424/60 |
| 2010/0178263 A1 | 7/2010 | Simonet et al. | |

FOREIGN PATENT DOCUMENTS

| | | |
|---|---|---|
| CN | 101061998 | 10/2007 |
| CN | 101791274 | 8/2010 |
| CN | 103079537 | 5/2013 |
| DE | 10 2004 030 886 A1 | 2/2006 |
| DE | 10 2007 060 528 A1 | 6/2009 |
| DE | 10 2009 027 963 A1 | 1/2011 |
| WO | 2009/074465 A2 | 6/2009 |
| WO | WO 2012/032055 | 3/2012 |
| WO | 2012/084337 A2 | 6/2012 |

OTHER PUBLICATIONS

International Search Report dated May 21, 2014 in PCT/BR13/000314 Filed Aug. 20, 2013.
Office Action dated Jul. 27, 2017, in Chinese Patent Application No. 201380079031.4 with English translation, 32 pages.

* cited by examiner

*Primary Examiner* — Jyothsna A Venkat
(74) *Attorney, Agent, or Firm* — Oblon, McClelland, Maier & Neustadt, L.L.P.

(57) ABSTRACT

The present invention relates to a cosmetic composition comprising one or more amino silicones, one or more cationic surfactants and one or more esters of formula R'—O—CO—R—CO—O—R". The invention also concerns a cosmetic treatment process for keratin substances, in particular for conditioning hair, implementing said cosmetic composition.

2 Claims, No Drawings

COSMETIC COMPOSITION COMPRISING AMINO SILICONES, CATIONIC SURFACTANTS AND SPECIFIC ESTERS AND A PROCESS FOR A COSMETIC TREATMENT

The present invention relates to a cosmetic composition, in particular a hair composition, comprising amino silicones, specific esters and cationic surfactants, and a cosmetic treatment process implementing it, in particular for conditioning hair.

Hair that has been sensitized, embrittled or indeed even damaged under the action of atmospheric agents or by mechanical and chemical treatments, such as dyeing operations, bleaching operations and/or perming operations, is often difficult to disentangle and to style and generally lacks softness. A solution to compensate for these problems is to use conditioning agents, in particular cationic surfactants, cationic polymers, fatty substances or silicones, to make hair easier to disentangle and to make it soft and supple. These conditioning agents improve the disentangling and softness of wet and dried hair, but may however have a tendency to make the hair lank and dull.

Haircare compositions such as rinse-off conditioners, and leave-on masks, creams and milks, are generally emulsions of varying degrees of thickness. They deliver good cosmetic properties to hair; however, users sometimes feel that their hair is heavy and that it becomes greasy easily, especially if they have fine hair. Additionally, it is sometimes difficult to know how much of these compositions to use, and users use lots of product for each application. It can also be difficult to distribute the composition evenly when applying it to the hair.

The object of the present invention is to propose a cosmetic composition having improved use properties and further delivering good conditioning properties to hair, in particular in terms of softness to the touch, suppleness, smoothness and disentangling.

One object of the present invention is therefore a cosmetic composition comprising one or more amino silicones, one or more cationic surfactants and one or more esters as defined hereafter.

It was observed that the composition has a creamy texture that feels pleasant and is easy to apply to hair; this composition spreads well on the hair and further rinses easily and quickly.

It gives the hair softness, smoothness and suppleness; it gives a natural healthy feel, particularly to sensitized, embrittled hair; it is particularly well suited to curly hair, and delivers supple and shiny curls; an apparent reduction in volume can also be observed, which allows better hair control.

In the present description, the term "at least one" is equivalent to the term "one or more" and may be replaced therewith; the term "between" is equivalent to the term "ranging from" and may be replaced therewith, which implies that the limits are included.

Amino Silicones

The cosmetic composition according to the invention comprises one or more amino silicones. The term "amino silicone" is intended to mean any silicone comprising at least one primary, secondary or tertiary amine or a quaternary ammonium group.

The weight-average molecular weights of these amino silicones can be measured by gel permeation chromatography (GPC) at room temperature (25° C.), as polystyrene equivalents. The columns used are p styragel columns. The eluent is THF and the flow rate is 1 ml/minute. 200 μl of a solution containing 0.5% by weight of silicone in THF are injected. Detection is performed by refractometry and UV-metry.

As amino silicone that may be used in the scope of this invention, the following can be cited:

(a) polysiloxanes corresponding to formula (A):

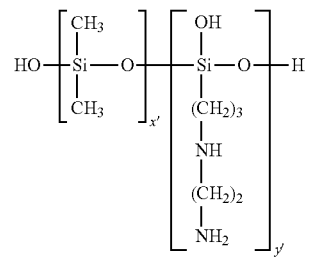

in which x' and y' are integers such that the weight-average molecular weight (Mw) is comprised between about 5000 and 500,000.

(b) amino silicones corresponding to formula (B):

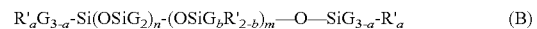

in which:

G, which may be identical or different, designate a hydrogen atom, or a phenyl, OH, $C_1$-$C_8$ alkyl group, for example methyl, or $C_1$-$C_8$ alkoxy, for example methoxy, a, which may be identical or different, denote the number 0 or an integer from 1 to 3, in particular 0, b denotes 0 or 1, and in particular 1, m and n are numbers such that the sum (n+m) ranges from 1 to 2000 and in particular from 50 to 150, it being possible for n to denote a number from 0 to 1999 and in particular from 49 to 149, and it being possible for m to denote a number from 1 to 2000 and in particular from 1 to 10;

$R^1$, which may be identical or different, denotes a monovalent radical having formula —$C_qH_{2q}$L in which q is a number ranging from 2 to 8 and L is an optionally quaternized amino group chosen from the following groups:

—NR"-Q-N(R")$_2$
—N(R")$_2$
—N$^+$(R")$_3$A-
N$^+$H(R")$_2$A-
N$^+$H$_2$(R") A-
N(R")-Q-N$^+$R"H$_2$A-
NR"-Q-N$^+$(R")$_2$H A-
NR"-Q-N$^+$(R")$_3$A-, in which R", which may be identical or different, denote a hydrogen, phenyl, benzyl, or a saturated monovalent hydrocarbon-based radical, for example a $C_1$-$C_{20}$ alkyl radical; Q denotes a linear or branched group having formula $C_rH_{2r}$, r being an integer ranging from 2 to 6, preferably from 2 to 4; and A- represents a cosmetically acceptable ion, in particular halide such as fluorine, chlorine, bromine or iodine.

A group of amino silicones corresponding to this definition (B) is represented by the silicones called "trimethylsilylamodimethicone" having formula (C):

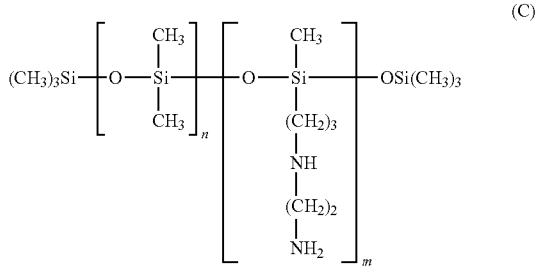

(C)

in which n and m have the meanings given above, in formula B.

Another group of amino silicones corresponding to this definition is represented by silicones having the following formulas (D) or (E):

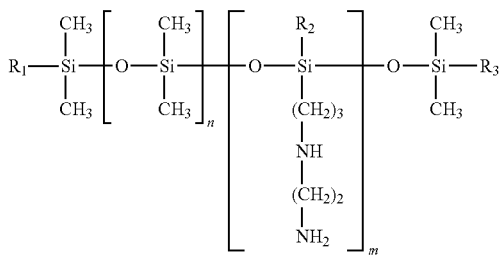

(D)

in which:
m and n are numbers such that the sum (n+m) ranges from 1 to 1000, in particular from 50 to 250 and more particularly from 100 to 200, it being possible for n to denote a number from 0 to 999 and in particular from 49 to 249, and more particularly from 125 to 175 and it being possible for m to denote a number from 1 to 1000 in particular from 1 to 10, and more particularly from 1 to 5;

R1, R2, R3, which may be identical or different, represent a hydroxy or $C_1$-$C_4$ alkoxy radical, where at least one of the radical R1 to R3 dew notes an alkoxy radical.

The alkoxy radical is preferably a methoxy radical.

The hydroxy/alkoxy molar ratio ranges preferably from 0.2:1 to 0.4:1 and preferably from 0.25:1 to 0.35:1 and more particularly equals 0.3:1. The weight-average molecular weight (Mw) of the silicone ranges preferably from 2000 to 1,000,000, more preferably from 3500 to 200,000.

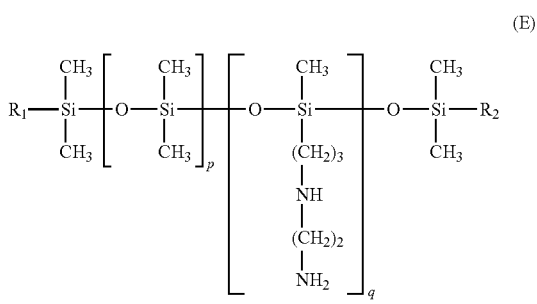

(E)

in which:
p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and it being possible for q to denote a number from 1 to 1000, in particular from 1 to 10, and more particularly from 1 to 5;

R1, R2, which may be different, represent a hydroxy or $C_1$-$C_4$ alkoxy radical, where at least one of the radical R1 or R2 denotes an alkoxy radical.

The alkoxy radical is preferably a methoxy radical.

The hydroxy/alkoxy molar ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200,000, even more preferably from 5000 to 100,000 and most preferably from 10,000 to 50,000.

Commercial products corresponding to these silicones having structure (D) or (E) may include in their composition one or more other amino silicones whose structure is different from formula (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or non-ionic. The average size in number of silicone particles in the emulsion generally ranges from 3 nm to 500 nanometers. Preferably, in particular as amino silicones having formula (E), microemulsions are used whose average particle size ranges from 5 nm to 60 nanometers (limits included) and more particularly from 10 nm to 50 nanometers (limits included). Thus, according to the invention microemulsions of amino silicone having formula (E) sold under the name Finish CT 96 E® or SLM 28020® by. Wacker can be used.

Another group of amino silicones corresponding to this definition is represented by the following formula (F):

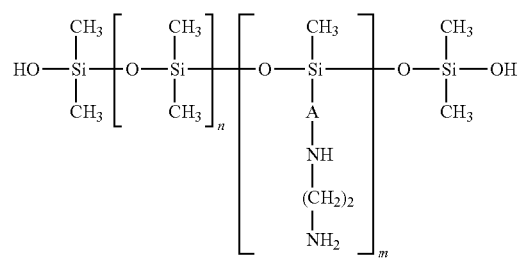

(F)

in which:
m and n are numbers such that the sum (n+m) ranges from 1 to 2000 and in particular from 50 to 150, it being possible for n to denote a number from 0 to 1999 and in particular from 49 to 149, and it being possible for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2,000 to 1,000,000 and even more preferably from 3,500 to 200,000.

A silicone corresponding to this formula is for example DC2-8566 Cationic Emulsion by Dow Corning.

Another group of amino silicones corresponding to this definition is represented by the following formula (G):

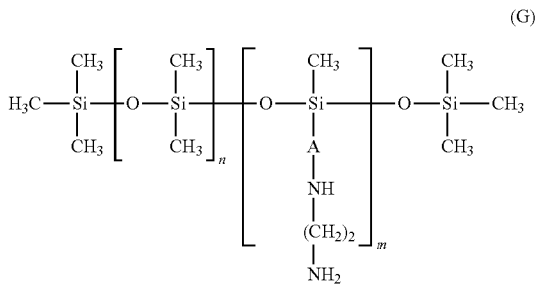

in which:
- m and n are numbers such that the sum (n+m) ranges from 1 to 2000 and in particular from 50 to 150, it being possible for n to denote a number from 0 to 1,999 and in particular from 49 to 149, and it being possible for m to denote a number from 1 to 2000 and in particular from 1 to 10;
- A denotes a linear or branched alkylene radical containing from 4 to 8 carbon atoms and preferably 4 carbon atoms. This radical is preferably branched. The weight-average molecular weight (Mw) of these amino silicones ranges preferably from 500 to 1,000,000 and even more preferably from 1000 to 200,000.

A silicone corresponding to this formula is for example DC2-8566 Amino Fluid by Dow Corning.

c) amino silicones corresponding to formula (H):

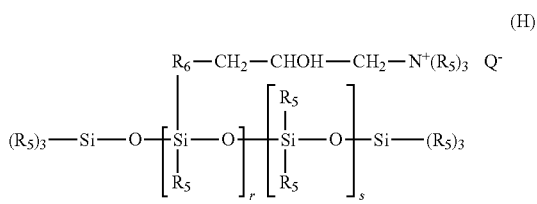

in which:
- $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;
- Q- is an anion such as a halide ion, in particular chloride, or an organic acid salt (acetate, etc.);
- r represents a mean statistical value from 2 to 20 and in particular from 2 to 8;
- s represents a mean statistical value from 20 to 200 and in particular from 20 to 50.

Such amino silicones are described more particularly in U.S. Pat. No. 4,185,087.

d) quaternary ammonium silicones having formula (I):

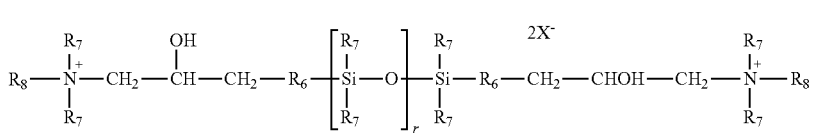

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;
- $X^-$ is an anion such as a halide ion, in particular chloride, or an organic acid salt (acetate, etc.);
- r represents a mean statistical value from 2 to 200 and in particular from 5 to 100;

These silicones are described, for example, in patent application EP-A 0 530 974.

e) amino silicones having formula (J):

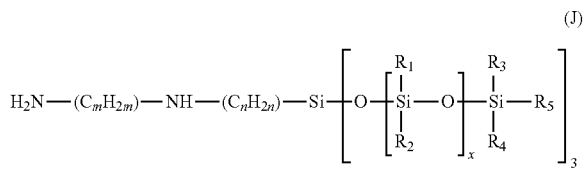

in which:
- $R_1$, $R_2$, $R_3$ and $R_4$, which may be identical or different, denote a $C_1$-$C_4$ alkyl radical or a phenyl group,
- $R_5$ denotes a $C_1$-$C_4$ alkyl radical or a hydroxyl group,
- n is an integer ranging from 1 to 5,
- m is an integer ranging from 1 to 5, and in which x is chosen such that the amine number ranges between 0.01 and 1 meq/g.

f) multiblock polyoxyalkylenated amino silicones, type (AB)n, A being a polysiloxane block and B being a polyoxyalkylenated block containing at least one amine group.

Said silicones are preferably constituted of repetitive units having the following general formulae:

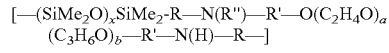

or alternatively

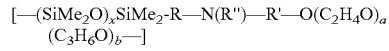

in which:
- a is an integer greater than or equal to 1, preferably ranging from 5 to 200, more particularly ranging from 10 to 100;
- b is an integer comprised between 0 and 200, preferably ranging from 4 to 100, more particularly ranging from 5 to 30;

x is an integer ranging from 1 to 10,000, more particularly from 10 to 5000.

R" is a hydrogen atom or a methyl;

R, which may be identical or different, represent a divalent linear or branched C2-C12 hydrocarbon-based radical, optionally including one or more heteroatoms such as oxygen; preferably, R denotes an ethylene radical, a linear or branched propylene radical, a linear or branched butylene radical, or a —CH2CH2CH2OCH(OH)CH2- radical; preferentially R denotes a —CH2CH2CH2OCH(OH)CH2- radical;

R', which may be identical or different, represent a divalent linear or branched C2-C12 hydrocarbon-based radical, optionally including one or more heteroatoms such as oxygen; preferably, R' denotes an ethylene radical, a linear or branched propylene radical, a linear or branched butylene radical, or a —CH2CH2CH2OCH(OH)CH2- radical; preferentially R' denotes —CH(CH3)-CH2-.

The siloxane blocks preferably represent between 50 and 95 mol % of the total weight of the silicone, more particularly from 70 to 85 mol %. The amine content is preferably comprised between 0.02 and 0.5 meq/g of copolymer in a 30% solution in dipropyleneglycol, more particularly between 0.05 and 0.2.

The weight-average molecular weight (Mw) of the silicone is preferably comprised between 5000 and 1,000,000, more particularly from 10000 to 200,000.

In particular, silicones sold as Silsoft A-843 or even Silsoft A+ by Momentive can be cited.

Preferably, the amino silicones are chosen from the multiblock polyoxyalkylenated amino silicones.

The composition according to the invention preferably comprises the amino silicone(s) in an amount ranging from 0.01% to 5% by weight, preferably from 0.02% to 2.5% by weight and preferentially from 0.05% to 1% by weight, relative to the total weight of the composition.

Cationic Surfactants

The cosmetic composition according to the invention also comprises one or more cationic surfactants. They are advantageously chosen from optionally polyoxyalkylenated primary, secondary or tertiary fatty amine salts, quaternary ammonium salts, and mixtures thereof.

As quaternary ammonium salts, mention may be made in particular of:

quaternary ammonium salts having formula (Ia) below:

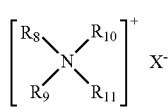

(Ia)

in which:

the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ containing from 8 to 30 carbon atoms and preferably from 12 to 24 carbon atoms; the aliphatic groups can comprise heteroatoms such as, in particular, oxygen, nitrogen, sulfur or halogens.

The aliphatic groups are chosen, for example, from $C_1$-$C_{30}$ alkyl, $C_1$-$C_{30}$ alkoxy, ($C_2$-$C_6$)polyoxyalkylene, $C_1$-$C_{30}$ alkylamide, ($C_{12}$-$C_{22}$)alkyl-($C_2C_6$)alkylamido, ($C_{12}$-$C_{22}$)alkyl acetate and $C_1$-$C_{30}$ hydroxyalkyl groups;

$X^-$ is an anion chosen from the group consisting of halides, phosphates, acetates, lactates, ($C_1$-$C_4$)alkylsulfates, ($C_1$-$C_4$) alkylsulfonates or ($C_1$-$C_4$)alkyl-arylsulfonates.

Among the quaternary ammonium salts having formula (Ia), preference is firstly given to tetraalkylammonium chlorides such as, for example, dialkyldimethylammonium or alkyltrimethylammonium chlorides in which the alkyl group comprises approximately from 12 to 22 carbon atoms, more particularly behenyltrimethylammonium, distearyldimethylammonium, cetyltrimethylammonium, and benzyldimethylstearylammonium chlorides, or secondly, to palmitylamidopropyltrimethylammonium chloride or stearamidopropyldimethyl(myristyl acetate)-ammonium chloride, in particular which is sold under the name Ceraphyl® 70 by the company Van Dyk.

imidazoline quaternary ammonium salts having formula (Ib):

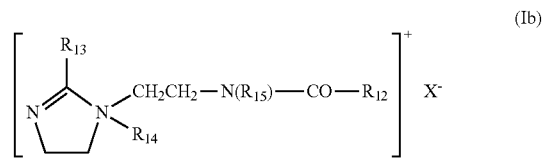

(Ib)

in which $R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ is an anion chosen from the group consisting of halides, phosphates, acetates, lactates, ($C_1$-$C_4$)alkylsulfates, ($C_1$-$C_4$)alkylsulfonates or ($C_1$-$C_4$)alkyl-arylsulfonates.

$R_{12}$ and $R_{13}$ preferably denote a mixture of alkyl or alkenyl groups containing from 12 to 21 carbon atoms, for example fatty acid derivatives of tallow, $R_{14}$ denotes a methyl group, and $R_{15}$ denotes a hydrogen atom. A product of this kind is sold for example under the name Rewoquat® W 75 by the company Rewo;

quaternary di- or triammonium salts having formula (IIIb):

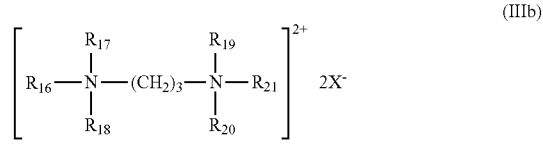

(IIIb)

in which $R_{16}$ denotes an alkyl group containing approximately from 16 to 30 carbon atoms, which is optionally hydroxylated and/or interrupted with one or more oxygen atoms, $R_{17}$ is chosen from hydrogen or an alkyl group containing from 1 to 4 carbon atoms or a group: —($CH_2$)$_3$—$N^+$($R_{16a}$)($R_{17a}$)($R_{18a}$), $R_{16a}$, $R_{17a}$, $R_{18a}$, $R_{18}$, $R_{19}$, $R_{20}$ et $R_{21}$, which may be identical or different, are chosen from hydrogen and an alkyl group comprising from 1 to 4 carbon atoms, and $X^-$ is an anion chosen from the group consisting of halides, acetates, phosphates, nitrates, $(C_1-C_4)$alkyl sulfates, $(C_1-C_4)$alkyl- or $(C_1-C_4)$alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions having the following formula (IVb):

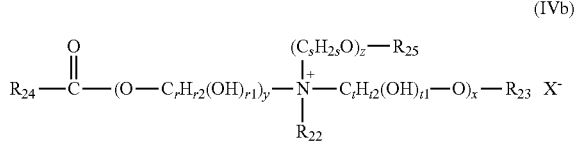

(IVb)

in which:

$R_{22}$ is chosen from $C_1-C_6$ alkyl groups and $C_1-C_6$ hydroxyalkyl or $C_1-C_6$ dihydroxyalkyl groups, $R_{23}$ is chosen from the group $R_{26}$—C(=O)—; hydrocarbon-based linear or branched, saturated or unsaturated $C_1-C_{22}$ groups $R_{27}$; and a hydrogen atom, $R_{25}$ is chosen from the group $R_{28}$—C(=O)—; hydrocarbon-based linear or branched, saturated or unsaturated $C_1-C_6$ groups $R_{29}$; and a hydrogen atom, $R_{24}$, $R_{26}$ and $R_{28}$, which may be identical or different, are chosen from linear or branched, saturated or unsaturated $C_7-C_{21}$ hydrocarbon-based groups, r, s and t, which may be identical or different, are integers ranging from 2 to 6, r1 and t1, which may be identical or different, are equal to 0 or 1, r2+r1=2 r and t1+t2=2 t, y is an integer ranging from 1 to 10, x and z, which may be identical or different, are integers ranging from 0 to 10, $X^-$ is a simple or complex, organic or inorganic anion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear. Preferably, $R_{22}$ denotes a methyl, ethyl, hydroxyethyl or dihydroxypropyl group, and more particularly a methyl or ethyl group.

Advantageously, the sum x+y+z has a value from 1 to 10.

When $R_{23}$ is an $R_{27}$ hydrocarbon-based group, it may be long and may have from 12 to 22 carbon atoms, or may be short and may have from 1 to 3 carbon atoms.

When $R_{25}$ is an $R_{29}$ hydrocarbon-based group, it preferably has 1 to 3 carbon atoms.

Advantageously, $R_{24}$, $R_{26}$ and $R_{25}$, which may be identical or different, are chosen from linear or branched, saturated or unsaturated $C_{11}-C_{21}$ hydrocarbon-based groups, and more particularly from linear or branched, saturated or unsaturated $C_{11}-C_{21}$ alkyl and alkenyl groups.

Preferably, x and z, which may be identical or different, are equal to 0 or 1. Advantageously, y is equal to 1. Preferably, r, s and t, which may be identical or different, are 2 or 3, and even more particularly they are 2.

The anion $X^-$ is preferably a halide, preferably chloride, bromide or iodide, a $(C_1-C_4)$alkyl sulfate or a $(C_1-C_4)$alkyl- or $(C_1-C_4)$alkylaryl-sulfonate.

However, it is possible to use methanesulfonate, phosphate, nitrate, tosylate, an anion derived from an organic acid, such as acetate or lactate, or any other anion that is compatible with the ammonium comprising an ester function.

The anion $X^-$ is even more particularly chloride, methyl sulfate or ethyl sulfate.

Use is made more particularly, in the composition according to the invention, of the ammonium salts having formula (IVb) in which:

$R_{22}$ denotes a methyl or ethyl group, x and y are equal to 1, z is equal to 0 or 1, r, s and t are equal to 2, $R_{23}$ is chosen from the group $R_{26}$—C(=O)—; methyl, ethyl or hydrocarbon-based $C_{14}-C_{22}$ groups; and a hydrogen atom, $R_{25}$ is chosen from the group $R_{28}$—C(=O)—; a hydrogen atom, $R_{24}$, $R_{26}$ and $R_{28}$, which may be identical or different, are chosen from linear or branched, saturated or unsaturated $C_{13}-C_{17}$ hydrocarbon-based groups, and preferably from linear or branched, saturated or unsaturated $C_{13}-C_{17}$ alkyl and alkenyl groups.

The hydrocarbon-based groups are advantageously linear.

Among the compounds of formula (IVb), examples that may be mentioned include the salts, in particular the chloride or the methyl sulfate of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil, such as palm oil or sunflower oil. When the compound comprises several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent, such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts. It is also possible to use the ammonium salts containing at least one ester function that are described in U.S. Pat. Nos. 4,874,554 and 4,137,180. Use may also be made of behenoylhydroxypropyltrimethylammonium chloride, for example, sold by the company Kao under the name Quartamin BTC 131.

Preferably, the ammonium salts containing at least one ester function contain two ester functions.

Preferably, the cationic surfactants are chosen from the cetyltrimethylammonium, behenyltrimethylammonium dipalmitoylethylhydroxyethylmethylammonium salts, and mixtures thereof, and more particularly from behenyltrimethylammonium chloride or methosulfate, cetyltrimethylammonium chloride, and dipalmitoylethylhydroxyethylammonium methosulfate, and mixtures thereof.

The composition according to the invention preferably comprises the cationic surfactant(s) in an amount ranging from 0.05% to 15% by weight, preferably from 0.1% to 10% by weight and preferentially from 0.2% to 5% by weight, relative to the total weight of the composition.

Esters

The cosmetic composition according to the invention also comprises one or more esters of formula (I):
wherein:
R represents a divalent, linear or branched, saturated or unsaturated C1-C10 hydrocarbon radical, eventually substituted by one or more hydroxyle groups (OH) and/or by one or more CO—O—R''' groups; with R''' representing an alkyle or alcenyle C8-C30 group, eventually substituted by one or more hydroxyle groups;
R' and R'', identical or different, represent an alkyle or alcenyle C8-C30 group, eventually substituted by one or more hydroxyle groups.

Preferably, R represents a divalent, linear or branched, saturated C1-C10 hydrocarbon radical, eventually substituted by one or two OH.

Preferably, R' and R'', identical or different, represent a C8-C30 alkyl group, most preferably a C10-C22 alkyl group, and further more a C12-C20 alkyl group.

Preferably, R' and R'' are identical.

As compounds of formula (I), mention may be made of:
dicaprylyl malate, diisostearyl malate, di(2-ethy hexyl) malate, dialkyl C12-C13 malate,
triisostearyl citrate, trioctyl dodecyl citrate, triisocetyle citrate, trioleyl citrate,
dialkyl C12-C13 tartrate, di(2-ethy hexyl) sebacate, di(2-ethy hexyl) succinate, diisocetyle dodecanedioate, diisostearyl adipate, diisononyl adipate.

In one embodiment, R is a saturated C1-C4 alkylene, linear or branched, radical, eventually substituted by one OH and/or by one COOR''' group; most preferably only eventually substituted by one OH group.

In another embodiment R' and R'', identical or different, represent an alkyle group, preferably a C10-C22 alkyle group.

Esters of formula (I) are preferably chosen from dialkyl C8-C30 malate, most preferably from dialkyl C10-C22 malate such as the product COSMACOL EMI sold by SASOL.

The composition according to the invention preferably comprises the ester(s) of formula (I) in an amount ranging from 0.01% to 15% by weight, preferably from 0.02% to 10% by weight and preferentially from 0.05% to 5% by weight, relative to the total weight of the composition.

Other Non-Silicone Fatty Substance

The cosmetic composition according to the invention may advantageously comprise one or more non-silicone fatty substances other than esters of formula (I).

"Fatty substance" means an organic compound that is insoluble in water at room temperature (25° C.) and at atmospheric pressure (1 atm), i.e. solubility of less than 5%, by weight, preferably less than 1% by weight. They are generally soluble in organic solvents under the same temperature and pressure conditions, for instance chloroform, ethanol, benzene, liquid petrolatum or decamethylcyclopentasiloxane.

The term "non-silicone fatty substance" means a fatty substance whose structure does not comprise any silicon atoms. The non-silicone fatty substances generally have in their structure a hydrocarbon-based chain comprising at least 6 carbon atoms and not comprising any siloxane groups.

Preferably, the composition may advantageously comprise one or more additional non-silicone fatty substances chosen from hydrocarbons, fatty alcohols, fatty acid and/or fatty alcohol esters different from esters of formula (I), fatty ethers, non-silicone waxes and mixtures thereof.

The non-silicone based fatty substances may be liquid or solid at room temperature and at atmospheric pressure (25° C., 1 atm).

As hydrocarbons that may be used, the following can be cited:
linear or branched, optionally cyclic C6-C16 alkanes; hexane, undecane, dodecane, tridecane, and isoparaffins, for instance isohexadecane, isododecane and isodecane can be cited.
linear or branched hydrocarbons composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene such as the product sold under the brand name Parleam® by the company NOF Corporation, and squalane.

The fatty alcohols that can be used may be liquid at 25° C., 1 atm, or may even be solid.

They are advantageously not glycerolated and not oxyalkylenated, and preferably include from 8 to 30 carbon atoms. They may be saturated or unsaturated.

The saturated liquid fatty alcohols are preferably branched. They can optionally comprise, in their structure, at least one aromatic or non-aromatic ring. They are preferably acyclic. Among the liquid saturated fatty alcohols, octyldodecanol, isostearyl alcohol, 2-hexyldecanol can be cited.

The unsaturated liquid fatty alcohols exhibit, in their structure, at least one double or triple bond and preferably one or more double bonds. When several double bonds are present, there are preferably 2 or 3 of them and they can be conjugated or non-conjugated. These unsaturated fatty alcohols can be linear or branched. They can optionally comprise, in their structure, at least one aromatic or non-aromatic ring. They are preferably acyclic. Among liquid unsaturated fatty alcohols, oleyl alcohol, linoleyl alcohol, linolenyl alcohol and undecylenyl alcohol can be cited.

The solid fatty alcohols that can be used are preferably chosen from linear or branched, saturated or unsaturated alcohols containing from 8 to 30 carbon atoms. Mention may be made, for example, of myristic alcohol, cetyl alcohol, stearyl alcohol and their mixture, cetylstearyl alcohol.

The liquid fatty esters are preferably esters from a $C_6$-$C_{32}$ fatty acid and/or a $C_6$-$C_{32}$ fatty alcohol, and are liquid at 25° C., 1 atm. Preferably, these are liquid esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. Preferably, for the esters of monoalcohols, at least one of the alcohol or the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; diethylene glycol diisononanoate.

Mention may also be made of sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides. Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose. The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds. The esters according to this variant may also be chosen from mono-, di-, tri- and tetraesters, and polyesters, and mixtures thereof. These esters may be, for example, oleates, laurates, palmitates, myristates, behenates, cocoates, stearates, linoleates, linolenates, caprates and arachidonates, and mixtures thereof, such as, in particular, oleopalmitate, oleostearate or palmitostearate mixed esters. More particularly, use is made of monoesters and diesters and in particular of sucrose, glucose or methylglucose mono- or dioleates, stearates, behenates, oleopalmitates, linoleates, linolenates or oleostearates. An example that may be mentioned is the product sold under the name Glucate® DO by the company Amerchol, which is a methylglucose dioleate.

Finally, use may also be made of natural or synthetic glycerol esters of mono-, di- or triacids. Among these, mention may be made of plant oils.

As oils of plant origin or synthetic triglycerides that may be used in the composition of the invention as liquid fatty esters, the following can be cited, for example, triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, caprylic/capric acid triglycerides, for instance those sold by the company Stearineries Dubois or those sold under the names Miglyol® 810, 812 and 818 by the company Dynamit Nobel, jojoba oil and shea butter oil.

The solid fatty acid esters and/or fatty alcohol esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The liquid fatty ethers may be chosen from liquid dialkyl ethers such as dicaprylyl ether. The non-liquid fatty ethers are preferably chosen from dialkyl ethers and in particular dicetyl ether and distearyl ether, alone or as a mixture.

The non-silicone waxes are chosen in particular from carnauba wax, candelilla wax, esparto wax, paraffin wax, ozokerite, plant waxes such as olive tree wax, rice wax, hydrogenated jojoba wax or absolute flower waxes, such as the blackcurrant blossom essential wax sold by Bertin (France), or animal waxes such as beeswaxes or modified beeswaxes (cerabellina), and ceramides.

The ceramides or ceramide analogues such as glycoceramides, which can be used in the compositions according to the invention, are known per se and are natural or synthetic molecules which may correspond to the general formula below:

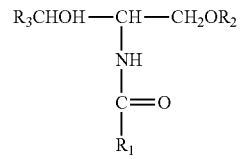

in which:
- $R_1$ denotes a linear or branched, saturated or unsaturated alkyl group which derives from $C_{14}$-$C_{30}$ fatty acids, it being possible for this group to be substituted in alpha position by a hydroxyl group, or in omega position by a hydroxyl group which is esterified with a saturated or unsaturated $C_{16}$-$C_{30}$ fatty acid;
- $R_2$ denotes a hydrogen atom or a (glycosyl)n, (galactosyl)m or sulfogalactosyl group, in which n is an integer ranging from 1 to 4 and m is an integer ranging from 1 to 8;
- $R_3$ denotes a $C_{15}$-$C_{26}$ hydrocarbon-based group which is saturated or unsaturated in alpha position, it being possible for this group to be substituted by one or more $C_1$-$C_{14}$ alkyl groups;

with the proviso that, in the case of natural ceramides or glycoceramides, $R_3$ may also denote a $C_{15}$-$C_{26}$ alpha-hydroxyalkyl group, the hydroxyl group being optionally esterified with a $C_{16}$-$C_{30}$ alpha-hydroxyacid.

The ceramide or ceramides that are more particularly preferred according to the invention are the compounds for which $R_1$ denotes a saturated or unsaturated alkyl derived from $C_{16}$-$C_{22}$ fatty acids; $R_2$ denotes a hydrogen atom; and $R_3$ denotes a saturated linear $C_{15}$ group. Such compounds are, for example, N-linoleyldihydrosphingosine, N-oleyldihydrosphingosine, N-palmityldihydrosphingosine, N-stearyldihydrosphingosine or N-behenyldihydrosphingosine, or mixtures of these compounds.

Preferentially, ceramides are used for which $R_1$ denotes a saturated or unsaturated alkyl group derived from $C_{14}$-$C_{30}$ fatty acids; $R_2$ denotes a galactosyl or sulfogalactosyl group; and $R_3$ denotes a CH=CH—$(CH_2)_{12}$—$CH_3$ group.

Preferably, the composition may comprise one or more additional non-silicone fatty substances chosen from hydrocarbons; $C_8$-$C_{30}$ saturated or unsaturated, liquid or non-liquid fatty alcohols; solid fatty esters; natural or synthetic glycerol esters of mono-, di or tri-acids and in particular triglyceride oils of plant origin; and ceramides.

In a more preferred manner, it may comprise one or more additional non-silicone fatty substances chosen from $C_8$-$C_{30}$ solid fatty alcohols such as myristic alcohol, cetyl alcohol, stearyl alcohol and cetylstearyl alcohol.

The composition may comprise the additional non-silicone fatty substance(s) in an amount preferably comprised between 0.25% and 15% by weight, in particular from 1% to 10% by weight and better still from 1.5% to 7.5% by weight, relative to the total weight of the composition.

Non-Ionic Surfactant

The composition according to the invention may advantageously comprise one or more non-ionic surfactants that may be chosen from alcohols, alpha-diols, (C1-C20)alkylphenols, these compounds being polyethoxylated, polypropoxylated or having a fatty chain including, for example, from 8 to 30 carbon atoms, in particular from 16 to 30 carbon atoms, where the number of ethylene oxide and/or propylene oxide groups may range in particular from 1 to 100, preferably from 2 to 50 and the number of glycerol groups may range in particular from 1 to 30, preferably from 2 to 30.

Mention may also be made of condensates of ethylene oxide and of propylene oxide with fatty alcohols; polyethoxylated fatty amides having preferably from 2 to 30 ethylene oxide units, polyglycerolated fatty amides containing on average from 1 to 5 glycerol groups, and particularly from 1.5 to 4; ethoxylated fatty acid esters of sorbitan having preferably from 2 to 40 ethylene oxide units, sucrose fatty acid esters, polyethylene glycol fatty acid esters, ethoxylated and/or propoxylated ethers of methylglucose; (C6-C24 alkyl)polyglycosides, N—(C6-C24 alkyl)glucamine derivatives, amine oxides such as (C10-C14 alkyl)amine oxides or N(C10-C14 acyl)aminopropylmorpholine oxides.

Preferentially (C6-C24 alkyl)polyglycosides, ethoxylated fatty acid esters of sorbitan, polyethoxylated fatty alcohols, ethoxylated and/or propoxylated ethers of methylglucose, and mixtures thereof are used.

The composition according to the invention preferably comprises the non-ionic surfactant(s) in an amount ranging from 0.05% to 8% by weight, preferably from 0.1% to 5% by weight and preferentially from 0.5% to 3% by weight, relative to the total weight of the composition.

Solvents

The composition according to the invention may advantageously comprise one or more organic solvents, advantageously liquid at 25° C., 1 atm., preferably hydrophilic (soluble or miscible in water) that may be chosen from $C_1$-$C_6$ aliphatic or aromatic monoalcohols, $C_2$-$C_8$ polyols, and $C_3$-$C_7$ polyol ethers. Advantageously, the organic solvent is chosen from $C_2$-$C_4$ mono-, di or tri-diols. It can advantageously be chosen from among ethanol, isopropanol, benzyl alcohol, glycerol, propane-1,2-diol (propylene glycol), dipropylene glycol, and mixtures thereof.

The composition may comprise the organic solvent(s) in an amount preferably ranging from 1 to 95% by weight, in particular from 5% to 80% by weight, and better still from 20% to 45% by weight, relative to the total weight of the composition.

The composition according to the invention may be provided in any conventionally used pharmaceutical form and in particular in the form of an aqueous, alcoholic or aqueous-alcoholic solution or suspension or oily solution or suspension; of a dispersion of the lotion or serum type; of an emulsion, in particular having a liquid or semi-liquid consistency, of the O/W, W/O or multiple type; of an aqueous or anhydrous gel, or of any other cosmetic form.

The composition according to the invention preferably comprises water at a concentration preferably ranging from 5% to 99% by weight, in particular from 20% to 98% by weight and better still from 40% to 95% by weight, relative to the total weight of the composition.

The pH of the composition, if it is aqueous, may be ranging from 3 to 8 and preferentially from 4 to 7.

The composition according to the invention may additionally comprise at least one or more common cosmetic ingredients different from those of the invention, chosen in particular from thickeners, gelling agents; polymers, in particular cationic polymers; sunscreens; moisturizers; anti-dandruff agents; antioxidants; chelating agents; reducing agents; oxidation bases, couplers, oxidizing agents, direct dyes; relaxants; nacreous agents and opacifiers; micas, nacres, glitter flakes; plasticizers or coalescers; hydroxy acids; pigments; fillers; fragrances; basifying or acidifying agents; silanes. A person skilled in the art will take care to choose the ingredients included in the composition and the amounts thereof so that they do not harm the properties of the compositions of the present invention.

The composition of the invention can be obtained by the mixture of two or more compositions, preferably two compositions, to form a ready to use composition.

The cosmetic composition according to the invention finds a particularly advantageous application in the hair sector, especially for caring for and/or for conditioning the hair. The haircare compositions are preferably conditioners, styling or treatment gels, treatment or conditioning lotions or creams, masks. Advantageously, the composition according to the invention is in the form of a conditioning product that can be rinsed off or left on.

The cosmetic composition may or may not be rinsed out after having been applied to the keratin substances, in particular hair. It is thus optionally possible to perform rinsing, for example with water, after an optional leave-in time. Preferably, it is rinsed out, after an optional leave-in time.

An object of the invention is also a cosmetic treatment process, especially for caring for and/or for conditioning keratin substances, in particular the hair, comprising the application to the said keratin substances of a cosmetic composition according to the invention, optionally followed by rinsing, after an optional leave-in time.

Preferably, this is a hair treatment process, particularly for caring for and/or conditioning hair, especially curly hair, or even sensitized, embrittled and/or damaged hair.

The present invention is illustrated in greater detail in the examples that follow (% AM=percentage of active material in the composition).

EXAMPLE 1

A hair composition for conditioning the hair is prepared the following manner:

First, a composition A comprising the following compounds is prepared:

| COMPOSITION A | % |
| --- | --- |
| CETRIMONIUM CHLORIDE | 1.85% |
| BEHENTRIMONIUM METHOSULFATE | 1.1% |
| MYRISTYL ALCOHOL | 3% |

-continued

| COMPOSITION A | % |
|---|---|
| CETEARYL ALCOHOL | 3.3% |
| DI-C12-13 ALKYL MALATE | 0.15% |
| CAPRYLIC/CAPRIC TRIGLYCERIDE | 3% |
| PEG-40/PPG-8 METHYLAMINOPROPYL/ HYDROXYPROPYL DIMETHICONE COPOLYMER | 0.89% |
| DIPROPYLENE GLYCOL | 0.33% |
| GLYCERIN | 1% |
| PROPYLENE GLYCOL | 14.8% |
| PPG-10 METHYL GLUCOSE ETHER | 0.89% |
| ETHANOL | 59% |
| PRESERVATIVE, FRAGRANCE | QS |
| WATER | QSP 100% |

Said composition A is then mixed with water, in a weight ratio composition A/water of 0.5.

The resulting composition corresponds to the composition of the invention.

It has a creamy texture that feels pleasant and is easy to apply to hair. This composition spreads well on the hair and further rinses easily and quickly. It gives the hair softness, smoothness and suppleness; it gives a natural healthy feel.

The invention claimed is:

1. A hair conditioning composition, comprising:
   from 20 to 80% by weight relative to the total weight of the composition of an alcohol selected from the group consisting of ethanol and isopropanol;
   water;
   from 0.01 to 5% by weight of PEG-40/PPG-8 methylaminopropyl hydroxypropyl dimethicone copolymer;
   from 0.2 to 5% by weight of cetyl trimethyl ammonium chloride;
   from 0.05 to 5% by weight of dialkyl C12-C13 malate;
   from 0.5 to 3% by weight of PPG-10 methyl glucose ether; and
   from 1.5 to 7.5% by weight of a mixture of cetearyl alcohol and myristyl alcohol:
   from 5% to 80% by weight relative to the total weight of the composition of at least one $C_1$-$C_6$ aliphatic mono-alcohol;
   from 5 to 20% by weight of water, relative to the total weight of the composition;
   one or more amino silicones;
   one or more cationic surfactants; and
   one or more esters of formula (I): R'—O—CO—R—CO—O—R" (I),
   wherein
   R represents a divalent, linear or branched, saturated or unsaturated C1-C10 hydrocarbon radical, substituted by one or more hydroxyl groups and/or by one or more CO—O—R''' groups; with R''' representing an alkyl or alkenyl C8-C30 group, substituted by one or more hydroxyl group, and
   R' and R", identical or different, represent an alkyl or alkenyl C8-C30 group, substituted by one or more hydroxyl groups,
   wherein the composition is capable of forming a cream when combined with water or a water-containing composition.

2. A method of conditioning the hair comprising applying a hair conditioning composition to hair according to claim 1.

* * * * *